US012622862B2

(12) United States Patent
Suthiwangcharoen et al.

(10) Patent No.: US 12,622,862 B2
(45) **Date of Patent: *May 12, 2026**

(54) HAIR CONDITIONER FORMULATION

(71) Applicants: Dow Global Technologies LLC, Midland, MI (US); Dow Silicones Corporation, Midland, MI (US); Rohm and Haas Company, Collegeville, PA (US)

(72) Inventors: Nisaraporn Suthiwangcharoen, Midland, MI (US); Lyndsay M. Leal, Spring City, PA (US); Michaeleen Pacholski, Collegeville, PA (US); Shannon Golden, Saginaw, MI (US); Emmett M. Partain, III, Bound Brook, NJ (US)

(73) Assignees: Dow Global Technologies LLC, Midland, MI (US); DOW SILICONES CORPORATION, Midland, MI (US); ROHM AND HAAS COMPANY, Collegeville, PA (US)

( * ) Notice: Subject to any disclaimer, the term of this patent is extended or adjusted under 35 U.S.C. 154(b) by 350 days.

This patent is subject to a terminal disclaimer.

(21) Appl. No.: 18/260,112

(22) PCT Filed: Mar. 9, 2022

(86) PCT No.: PCT/US2022/019466

§ 371 (c)(1),
(2) Date: Jun. 30, 2023

(87) PCT Pub. No.: WO2022/203863

PCT Pub. Date: Sep. 29, 2022

(65) Prior Publication Data

US 2024/0091123 A1 Mar. 21, 2024

Related U.S. Application Data

(60) Provisional application No. 63/164,059, filed on Mar. 22, 2021.

(51) Int. Cl.
*A61K 8/73* (2006.01)
*A61K 8/41* (2006.01)
*A61Q 5/12* (2006.01)

(52) U.S. Cl.
CPC ................ *A61K 8/73* (2013.01); *A61K 8/416* (2013.01); *A61Q 5/12* (2013.01); *A61K 2800/5426* (2013.01)

(58) Field of Classification Search
CPC .. A61K 8/73; A61K 8/416; A61K 2800/5426; A61Q 5/12
See application file for complete search history.

(56) References Cited

U.S. PATENT DOCUMENTS

| | | | | |
|---|---|---|---|---|
| 4,411,891 | A * | 10/1983 | Mizutani | A61Q 5/00 424/70.13 |
| 5,120,531 | A * | 6/1992 | Wells | A61K 8/8182 424/70.17 |
| 8,518,387 | B2 | 8/2013 | Drovetskaya et al. | |
| 9,493,398 | B2 * | 11/2016 | Deavenport | D06P 5/225 |
| 10,633,683 | B2 | 4/2020 | Paullin et al. | |
| 10,716,748 | B2 | 7/2020 | Gonzalez et al. | |
| 10,874,598 | B2 | 12/2020 | Yang et al. | |
| 12,396,939 | B2 * | 8/2025 | O'Connor | C08L 5/02 |
| 2008/0003192 | A1 | 1/2008 | Modi | |
| 2010/0093584 | A1 | 4/2010 | Brand et al. | |
| 2010/0247472 | A1 | 9/2010 | Sau | |
| 2011/0177017 | A1 | 7/2011 | Coffindaffer et al. | |
| 2015/0098920 | A1 | 4/2015 | Stella et al. | |
| 2015/0203598 | A1 | 7/2015 | Landschutze et al. | |
| 2018/0237816 | A1 | 8/2018 | Paullin et al. | |

FOREIGN PATENT DOCUMENTS

| | | |
|---|---|---|
| CN | 106511133 | 3/2017 |
| DE | 10018158 | 10/2001 |
| EP | 2119428 | 11/2009 |
| EP | 3486356 | 5/2019 |

(Continued)

OTHER PUBLICATIONS

Mintel, "Chinese Medicine Anti-Dandruff & Olive Moisturising Shampoo", Bawang Cosmetic, 2015, Database GNPD, CN.
Mintel, "Refresh Mint Cool Body Wash Gel", Bawang Cosmetic, 2015, Database GNPD, CN.
Sibilia "A Guide to Materials Characterization and Chemical Analysis", VCH, 1988, pp. 81-84.

(Continued)

*Primary Examiner* — Sahana S Kaup
*Assistant Examiner* — Toriana N. Vigil
(74) *Attorney, Agent, or Firm* — Thomas S. Deibert

(57) ABSTRACT

A hair conditioner formulation is provided, comprising: a dermatologically acceptable vehicle; and a conditioning polymer, wherein the conditioning polymer is a dextran polymer crosslinked with a dextran crosslinking agent of formula (I) wherein X is a halogen; wherein each $R^1$ is independently selected from a substituted or unsubstituted $C_{1-6}$ alkyl group; wherein each $R_2$ is independently selected from the group consisting of a $C_{1-6}$ alkanediyl group; wherein Y is a divalent bridging group.

(I)

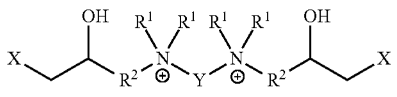

10 Claims, No Drawings

(56) References Cited

FOREIGN PATENT DOCUMENTS

| | | |
|---|---|---|
| JP | 10279449 | 10/1998 |
| JP | 11322555 | 11/1999 |
| JP | 2000159642 | 6/2000 |
| JP | 2000319139 | 11/2000 |
| JP | 3720964 | 11/2005 |
| JP | 2009062281 | 3/2009 |
| JP | 4712222 | 6/2011 |
| WO | 2010009938 | 1/2010 |
| WO | 2010089228 | 8/2010 |
| WO | 2014047099 | 3/2014 |
| WO | 2017174678 | 10/2017 |
| WO | 2021194804 | 9/2021 |
| WO | 2021194805 | 9/2021 |
| WO | 2021194807 | 9/2021 |
| WO | 2021194809 | 9/2021 |

OTHER PUBLICATIONS

STANCIU "Influence of dextran hydrogel characteristics on adsorption capacity for anionic dyes", Carbohydrate Polymers, 2018, pp. 75-83, vol. 199, Applied Science Publishers, LTD Barking, GB.

Yau, "Modern Size Exclusion Chromatography", Wiley-Interscience, 1979.

* cited by examiner

HAIR CONDITIONER FORMULATION

The present invention relates to a hair conditioner formulation. In particular, the present invention relates to a hair conditioner formulation, comprising: a dermatologically acceptable vehicle; and a conditioning polymer, wherein the conditioning polymer is a dextran polymer crosslinked with a dextran crosslinking agent of formula (I)

(I)

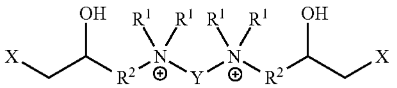

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group.

Conventional hair conditioners are popular with consumers for treating hair. Silicone based conditioning agents are the most commonly used conditioning agent in hair conditioner formulations. However, there are growing concerns among some consumers regarding the persistence and potential toxicity of certain silicone based conditioning agents in the environment, particularly for D4 and D5 conditioners. Accordingly, there has been a growing interest in the development of silicone-free alternative conditioning agents for use in hair conditioner formulations.

In U.S. Pat. No. 5,879,670, Melby et al disclose a non-silicon containing amphyolyte polymer for use as a conditioning agent for treatment of a keratin-containing substrate. In particular, Melby et al disclose novel conditioning polymer containing (meth)acrylamidopropyltrimethyl ammonium chloride, meth(acrylic acid) or 2-(meth)acrylamido-2-methylpropane sulfonic acid and, optionally, a $C_{1-22}$ alkyl (meth)acrylate and the use thereof in a cosmetically acceptable medium for the treatment of a keratin-containing substrate.

Notwithstanding, there is a continuing need for new hair conditioning agents that provide conditioning benefits. There is also a continuing need for new hair conditioning agents having an increased natural origin index (IS016128) when compared with conventional hair conditioning agents.

The present invention provides a hair conditioner formulation, comprising: a dermatologically acceptable vehicle; and a conditioning polymer, wherein the conditioning polymer is a dextran polymer crosslinked with a dextran crosslinking agent of formula (I)

(I)

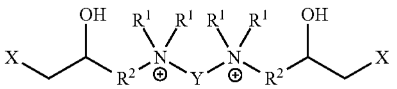

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group.

The present invention provides a hair conditioner formulation, comprising: a dermatologically acceptable vehicle; and a conditioning polymer, wherein the conditioning polymer is a dextran polymer crosslinked with a dextran crosslinking agent of formula (I)

(I)

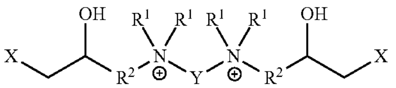

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group; and wherein the hair conditioner formulation contains less than 0.01 wt %, based on weight of the hair conditioner formulation, of a dermatologically acceptable oil.

The present invention provides a hair conditioner formulation, comprising: a dermatologically acceptable vehicle; and a conditioning polymer, wherein the conditioning polymer is a dextran polymer crosslinked with a dextran crosslinking agent of formula (I)

(I)

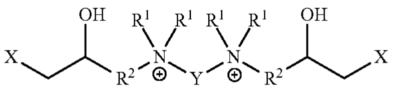

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group; and wherein the hair conditioner formulation contains less than 0.1 wt %, based on weight of the hair conditioner formulation, of silicon containing molecules.

The present invention provides a hair conditioner formulation, comprising: a dermatologically acceptable vehicle; and a conditioning polymer, wherein the conditioning polymer is a dextran polymer crosslinked with a dextran crosslinking agent of formula (I)

(I)

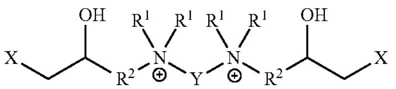

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group; wherein the hair conditioner formulation contains less than 0.01 wt %, based on weight of the hair conditioner formulation, of a dermatologically acceptable oil; and wherein the hair conditioner formulation contains less than 0.1 wt %, based on weight of the hair conditioner formulation, of silicon containing molecules.

The present invention provides a method of conditioning mammalian hair, comprising: selecting a hair conditioner formulation of the present invention; and applying the hair conditioner formulation to mammalian hair.

DETAILED DESCRIPTION

We have surprisingly found that dextran polymer crosslinked with a dextran crosslinking agent of formula (I)

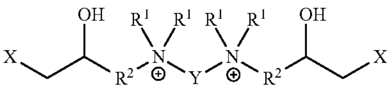
(I)

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group; acts as a conditioning polymer that effectively restores hydrophobicity to damaged hair and reduces the force required to comb treated hair.

Unless otherwise indicated, ratios, percentages, parts, and the like are by weight.

As used herein, unless otherwise indicated, the phrase "molecular weight" or $M_W$ refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the hair conditioner formulation of the present invention is selected from the group consisting of a conditioning shampoo formulation, a rinse off conditioner formulation and a leave on conditioner formulation. More preferably, the hair conditioner formulation of the present invention is selected from the group consisting of a rinse off conditioner formulation and a leave on conditioner formulation. Most preferably, the hair conditioner formulation of the present invention is a rinse off conditioner formulation.

Preferably, the hair conditioner formulation of the present invention, comprises: a dermatologically acceptable vehicle (preferably, wherein the hair conditioner formulation comprises 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle); and a conditioning polymer (preferably, wherein the hair conditioner formulation comprises 0.1 to 1 wt % (preferably, 0.15 to 0.75 wt %; more preferably, 0.2 to 0.5 wt %; most preferably, 0.25 to 0.4 wt %), based on weight of the hair conditioner formulation, of a tertiary amine functionalized dextran polymer), wherein the conditioning polymer is a dextran polymer crosslinked with a dextran crosslinking agent of formula (I)

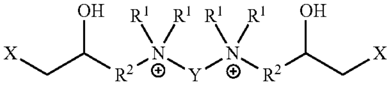

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group; and wherein the conditioning polymer enhances deposition of the dermatologically acceptable silicone from the hair conditioner formulation onto mammalian hair.

Preferably, the hair conditioner formulation of the present invention is a liquid formulation. More preferably, the hair conditioner formulation of the present invention is an aqueous liquid formulation.

Preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle. More preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle; wherein the dermatologically acceptable vehicle comprises water. Still more preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle; wherein the dermatologically acceptable vehicle is selected from the group consisting of water and an aqueous $C_{1-4}$ alcohol mixture. Most preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle; wherein the dermatologically acceptable vehicle is water.

Preferably, the water used in the hair conditioner formulation of the present invention is at least one of distilled water and deionized water. More preferably, the water used in the hair conditioner formulation of the present invention is distilled and deionized.

Preferably, the hair conditioner formulation of the present invention comprises 0.1 to 1 wt % (preferably, 0.15 to 0.75 wt %; more preferably, 0.2 to 0.5 wt %; most preferably, 0.25 to 0.4 wt %), based on weight of the hair conditioner formulation, of a conditioning polymer; wherein the conditioning polymer is a dextran polymer crosslinked with a dextran crosslinking agent of formula (I). More preferably, the hair conditioner formulation of the present invention comprises 0.1 to 1 wt % (preferably, 0.15 to 0.75 wt %; more preferably, 0.2 to 0.5 wt %; most preferably, 0.25 to 0.4 wt %), based on weight of the hair conditioner formulation, of a conditioning polymer; wherein the conditioning polymer is a dextran polymer crosslinked with a dextran crosslinking agent of formula (I); wherein the conditioning polymer has a Kjeldahl nitrogen content corrected for ash and volatiles, TKN, of 0.5 to 5.0 wt % (preferably, 0.75 to 4 wt %; more preferably, 1 to 3.5 wt %; most preferably, 1.5 to 3.0 wt %) (measured using a Buchi KjelMaster K-375 automated analyzer, corrected for volatiles and ash measured as described in ASTM method D-2364).

Preferably, the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons). More preferably, the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons); and the dextran polymer is a branched chain dextran polymer comprising a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages. Most preferably, the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons); and the dextran polymer is a branched chain dextran polymer comprising a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages according to formula II (II)

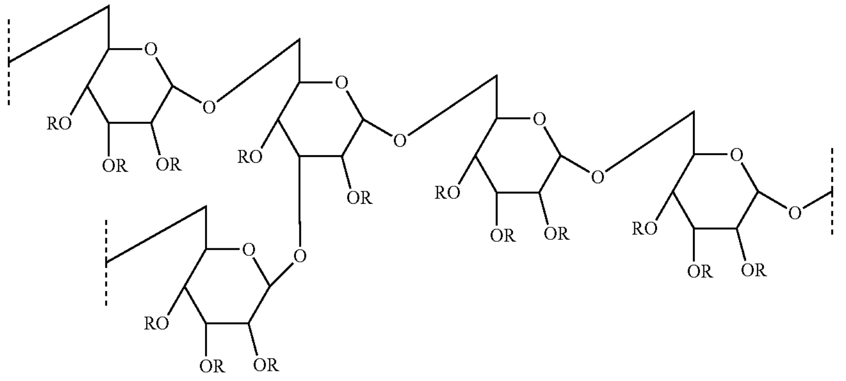

wherein R is selected from a hydrogen, a $C_{1-4}$ alkyl group and a hydroxy $C_{1-4}$ alkyl group; and wherein the average branch off the dextran polymer backbone is ≤3 anhydroglucose units.

Preferably, the dextran polymer contains less than 0.01 wt %, based on weight of the dextran polymer, of alternan. More preferably, the dextran polymer contain less than 0.001 wt %, based on weight of the dextran polymer, of alternan. Most preferably, the dextran polymer contains less than the detectable limit of alternan.

Preferably, the conditioning polymer is a dextran polymer crosslinked with a dextran crosslinking agent of formula (I)

(I)

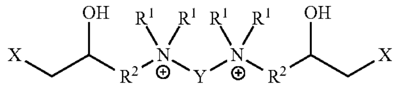

wherein X is a halogen (preferably, wherein each X is independently selected from the group consisting of —Cl, —Br and —I; more preferably, wherein each X is a —Cl); wherein each $R^1$ is independently selected from a substituted or unsubstituted $C_{1-6}$ alkyl group (wherein "substituted" means that the group in question contains at least one moiety selected from a halogen, a hydroxy group, an amino group or a carboxy group) (preferably, wherein each $R^1$ is independently selected from an unsubstituted $C_{1-6}$ alkyl group; more preferably, wherein each $R^1$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^1$ is independently selected from the group consisting of a methyl group, an ethyl group, a propyl group, an isopropyl group, a butyl group, an isobutyl group, a tert-butyl group and a sec-butyl group; yet more preferably, wherein each $R^1$ is independently selected from the group consisting of a methyl group, an ethyl group, a propyl group and an isopropyl group; yet still more preferably, wherein each $R^1$ is independently selected from the group consisting of a methyl group and an ethyl group; most preferably, wherein each $R^1$ is a methyl group); wherein each $R^2$ is independently selected from the group consisting of a $C_{1-6}$ alkanediyl group (preferably, a $C_{1-4}$ alkanediyl group; more preferably, a $C_{1-2}$ alkanediyl group; most preferably, a —$CH_2$— group); and wherein Y is a divalent bridging group (preferably, a $C_{1-6}$ alkanediyl group and a —$R^3$—O—$R^4$— group (more preferably, a —$R^3$—O—$R^4$— group); wherein $R^3$ and $R^4$ are independently selected from the group consisting of a $C_{1-6}$ alkanediyl group (preferably, a $C_{1-4}$ alkanediyl group; more preferably, a $C_{1-3}$ alkanediyl group; most preferably, a —$CH_2CH_2$— group)(preferably, $R^3$ and $R^4$ are the same). More preferably, the conditioning polymer is a dextran polymer crosslinked with a dextran crosslinking agent of formula (I); wherein the dextran crosslinking agent of Formula (I) is of Formula (II)

(II)

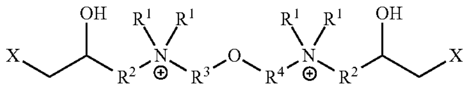

wherein X is a halogen (preferably, wherein each X is independently selected from the group consisting of —Cl, —Br and —I; more preferably, wherein each X is a —Cl); wherein each $R^1$ is independently selected from a substituted or unsubstituted $C_{1-6}$ alkyl group (wherein "substituted" means that the group in question contains at least one moiety selected from a halogen, a hydroxy group, an amino group or a carboxy group) (preferably, wherein each $R^1$ is independently selected from an unsubstituted $C_{1-6}$ alkyl group; more preferably, wherein each $R^1$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^1$ is independently selected from the group consisting of a methyl group, an ethyl group, a propyl group, an isopropyl group, a butyl group, an isobutyl group, a tert-butyl group and a sec-butyl group; yet more preferably, wherein each $R^1$ is independently selected from the group consisting of a methyl group, an ethyl group, a propyl group and an isopropyl group; yet still more preferably, wherein each $R^1$ is independently selected from the group consisting of a methyl group and an ethyl group; most preferably, wherein each $R^1$ is a methyl group); wherein each $R^2$ is independently selected from the group consisting of a $C_{1-6}$ alkanediyl group (preferably, a $C_{1-4}$ alkanediyl group; more preferably, a $C_{1-2}$ alkanediyl group; most preferably, a $—CH_2—$ group); and wherein $R^3$ and $R^4$ are independently selected from the group consisting of a $C_{1-6}$ alkanediyl group (preferably, a $C_{1-4}$ alkanediyl group; more preferably, a $C_{1-3}$ alkanediyl group; most preferably, a $—CH_2CH_2—$ group) (preferably, $R^3$ and $R^4$ are the same). Most preferably, the conditioning polymer is a dextran polymer crosslinked with a dextran crosslinking agent of formula (I) selected from the group consisting of

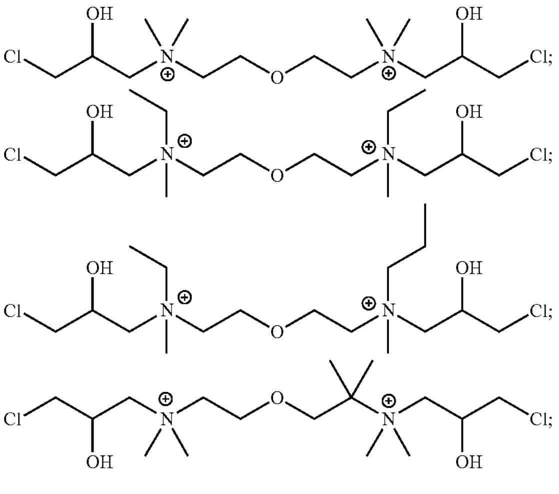

and mixtures thereof.

Preferably, the conditioning polymer comprises <0.001 meg/gram (preferably, <0.0001 meq/gram; more preferably, <0.00001 meq/gram; most preferably, <detectable limit) of aldehyde functionality.

Preferably, the conditioning polymer comprises <0.1% (preferably, <0.01%; more preferably, <0.001%; most preferably, <detectable limit), of the linkages between individual glucose units in the conditioning polymer are β-1,4 linkages.

Preferably, the conditioning polymer comprises <0.1% (preferably, <0.01%; more preferably, <0.001%; most preferably, <detectable limit), of the linkages between individual glucose units in the conditioning polymer are β-1,3 linkages.

Preferably, the conditioning polymer comprises <0.001 meq/gram (preferably, <0.0001 meq/gram; more preferably, <0.00001 meq/gram; most preferably, <detectable limit) of silicone containing functionality.

Preferably, the hair conditioner formulation of the present invention contains <0.01 wt % (preferably, <0.001 wt %; more preferably, <0.0001 wt %; most preferably, <detectable limit), based on weight of the hair conditioner formulation of a dermatologically acceptable oil. More preferably, the hair conditioner formulation of the present invention contains <0.01 wt % (preferably, <0.001 wt %; more preferably, <0.0001 wt %; most preferably, <detectable limit), based on weight of the hair conditioner formulation of a dermatologically acceptable oil; wherein the dermatologically acceptable oil is selected from the group consisting of hydrocarbon oils (e.g., mineral oil, petroleum jelly, polyisobutene, hydrogenated polyisobutene, hydrogenated polydecene, polyisohexadecane; natural oils (e.g., caprylic and capric triglyceride, sunflower oil, soybean oil, coconut oil, argan oil, olive oil, almond oil); fragrance oils (e.g., limonene) and mixtures thereof.

Preferably, the hair conditioner formulation of the present invention contains <0.1 wt % (preferably, <0.001 wt %; more preferably, <0.0001 wt %; most preferably, <detectable limit), based on weight of the hair conditioner formulation, of silicones (e.g., polydimethylsiloxanes, dimethicones, cyclodimethicones, aminosilicones).

Preferably, the hair conditioner formulation of the present invention contains <0.1 wt % (preferably, <0.001 wt %; more preferably, <0.0001 wt %; most preferably, <detectable limit), based on weight of the hair conditioner formulation, of silicon (Si) containing molecules.

Preferably, the hair conditioner formulation of the present invention, optionally, further comprises at least one additional ingredient selected from the group consisting of an antimicrobial agent/preservative (e.g., benzoic acid, sorbic acid, phenoxyethanol, methylisothiazolinone); a rheology modifier (e.g., hydroxyethyl cellulose, PEG-150 pentaerythrityl tetrastearate); a soap; a colorant; pH adjusting agent; an antioxidant (e.g., butylated hydroxytoluene); a humectant (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), triols, cationic polymeric polyols); a wax; a foaming agent; an emulsifying agent; a colorant; a fragrance; a chelating agent (e.g., tetrasodium ethylene diamine tetraacetic acid); a preservative (e.g., benzoic acid, sorbic acid, phenoxyethanol, methylisothiazolinone); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an anti-static agent; an anti-frizz agent; an antidandruff agent; a hair waving/straightening agent; a hair styling agent; an absorbent; a hard particle; a soft particle; a conditioning agent (e.g., guar hydroxypropyltrimonium chloride, PQ-10, PQ-7); a slip agent; an opacifier; a pearlizing agent and a salt. More preferably, the hair conditioner formulation of the present invention, optionally, further comprises at least one additional ingredient selected from the group consisting of an antimicrobial agent/preservative (e.g., benzoic acid, sorbic acid, phenoxyethanol, methylisothiazolinone); a rheology modifier (e.g., hydroxyethyl cellulose, PEG-150 pentaerythrityl tetrastearate); and a chelating agent (e.g., tetrasodium ethylene diamine tetraacetic acid). Most preferably, the hair conditioner formulation of the present invention, optionally, further comprises at least one additional ingredient selected from the group consisting of a hydroxyethyl cellulose; a tetrasodium ethylene diamine tetraacetic acid; a combination of phenoxyethanol and methylisothiazolinone; and mixtures thereof.

Preferably, the hair conditioner formulation of the present invention further comprises a thickener. More preferably, the hair conditioner formulation further comprises a thickener, wherein the thickener is selected to increase the viscosity of the hair conditioner formulation, preferably without substantially modifying the other properties of the hair conditioner formulation. Preferably, the hair conditioner formulation of the present invention further comprises 0 to 5.0 wt % (preferably, 0.1 to 5.0 wt %; more preferably, 0.2 to 2.5 wt %; most preferably, 0.5 to 2.0 wt %), based on weight of the hair conditioner formulation, of a thickener; wherein the thickener is selected to increase the viscosity of the hair conditioner formulation (preferably without substantially modifying the other properties of the hair conditioner formulation). More preferably, the hair conditioner formulation of the present invention further comprises 0.1 to 5.0 wt % (preferably, 0.2 to 2.5 wt %; more preferably, 0.5 to 2.0 wt %), based on weight of the hair conditioner formulation, of a thickener; wherein the thickener includes a hydroxyethyl cellulose. Most preferably, the hair conditioner formulation of the present invention further comprises 0.1 to 5.0 wt % (preferably, 0.2 to 2.5 wt %; more preferably, 0.5 to 2.0 wt %), based on weight of the hair conditioner formulation, of a thickener; wherein the thickener is hydroxyethyl cellulose.

Preferably, the hair conditioner formulation of the present invention further comprises an antimicrobial agent/preservative. More preferably, the hair conditioner formulation of the present invention further comprises an antimicrobial/preservative, wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Still more preferably, the hair conditioner formulation of the present invention, further comprises an antimicrobial/preservative, wherein the antimicrobial/preservative is a mixture of phenoxyethanol and an isothiazolinone (more preferably, wherein the antimicrobial/preservative is a mixture of phenoxyethanol and methylisothiazolinone).

Preferably, the hair conditioner formulation of the present invention optionally further comprises a pH adjusting agent. More preferably, the hair conditioner formulation of the present invention, further comprises a pH adjusting agent, wherein the hair conditioner formulation has a pH of 4 to 9 (preferably, 4.25 to 8; more preferably, 4.5 to 7; most preferably, 4.75 to 6).

Preferably, the pH adjusting agent is selected from the group consisting of at least one of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of at least one of citric acid, lactic acid, sodium hydroxide, potassium hydroxide, triethanolamine, amino-2-methyl-1-propanol. Still more preferably, the pH adjusting agent includes citric acid. Most preferably, the pH adjusting agent is citric acid.

Preferably, the method of conditioning mammalian hair of the present invention comprises: selecting a hair conditioner formulation of the present invention and applying the hair conditioner formulation to mammalian hair. Preferably, the method of conditioning mammalian hair of the present invention, further comprises: wetting the hair with water before applying the hair conditioner. Most preferably, the method of conditioning mammalian hair of the present invention, comprises: selecting a hair conditioner formulation of the present invention; wetting mammalian hair; and applying the hair conditioner formulation to the wetted mammalian hair.

Some embodiments of the present invention will now be described in detail in the following Examples.

Example S1: Synthesis of Dextran Crosslinking Agent

Bis [2-(N,N-dimethyamino)ethyl]ether (10.84 g) and water (23.12 g) were mixed together in a container. The pH of the container contents were pH adjusted to 8.5 with concentrated hydrochloric acid. The set point temperature for the container contents was maintained at 25° C. while 99.9% epichlorohydrin (20.84 g) was added to the container over a period of 60 minutes. The set point temperature of the container contents was maintained at 25° C. for an additional 2 hours, before raising the set point temperature to 50° C. and maintaining that temperature set point for 2 hours. The pH of the container contents was then lowered to <2.0 with concentrated hydrochloric acid and the set point temperature was increased to 70° C. and maintaining that temperature set point for an hour. The container contents were then cooled. After the temperature of the container contents fell below 50° C., the pH of the container contents was adjusted to 4-6 with 50% sodium hydroxide solution. An extraction of the container contents was then performed with methylene chloride seven times (1 vol:1 vol), then the residual methylene chloride was removed conventionally. The recovered material contained 39.4 wt % product solids. The product solids were analyzed via $^{13}C$ NMR to confirm the product was

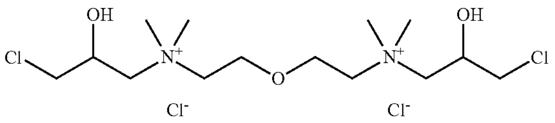 [SMILES: C[N+](C)(CCOCC[N+](C)(C)CC(O)CCl)CC(O)CCl ; [Cl-] ; [Cl-]]

N,N'-(oxybis(ethane-2,1-diyl))bis(3-chloro-2-hydroxy-N, N-dimethylpropan-1-aminium) chloride.

Example S2: Synthesis of Crosslinked Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran (23.23 g; Aldrich product #D4876) and deionized water (120 g). The weight average molecular weight of the dextran was 100,000 to 200,000 Daltons. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 50% aqueous sodium hydroxide solution (14.9 g) was added over a period of a few minutes to the flask contents with stirring under nitrogen. The flask contents were then allowed to stir under nitrogen for 30 minutes. Then a 47% aqueous solution of a dextran crosslinking agent prepared according to Examples S1 (74.45 g) was added to the flask contents and allowed to stir for five minutes prior to heating. Then heat was applied to the flask contents with a heating mantle controlled using the J-KEM controller set at 55° C. The flask contents were heated to and maintained at 55° C. for 90 minutes. The flask contents were then cooled to room temperature while maintaining a positive nitrogen pressure in the flask. When the flask contents reached room temperature, the flask contents were neutralized by adding glacial acetic acid (3.0 g) and the flask contents were allowed to stir for ten minutes. The flask contents were then diluted and transferred without purification for use; the diluted product solids content was 11.1 wt %. An aliquot of the solution was precipitated from methanol and dried in vacuo at 50° C. The total Kjeldahl nitrogen content, TKN, of the dried precipitate was measured using a Buchi KjelMaster K-375 automated analyzer at 2.72 wt %.

Comparative Examples CF1-CF3 and Example F1: Rinse Off Conditioner Formulations Rinse off conditioner formulations were prepared in each of Comparative Examples CF1-CF3 and Example F1 having the formulation noted in Table 1.

TABLE 1

| Ingredient INCI name | CF1 | CF2 | CF3 | F1 |
|---|---|---|---|---|
| | wt % active | | | |
| Deionized water | q.s. 100 | | | |
| Polyquaternium-10[1] | 0 | 0 | 0.3 | 0 |
| Unmodified branched chain dextran[2] | 0 | 0.3 | 0 | 0 |
| Crosslinked dextran polymer-Example S2 | 0 | 0 | 0 | 0.3 |
| Tetrasodium EDTA[3] | 0.2 | 0.2 | 0.2 | 0.2 |
| Hydroxyethyl cellulose[4] | 1.4 | 1.4 | 1.4 | 1.4 |
| Cetearyl alcohol[5] | 1 | 1 | 1 | 1 |
| Glyceryl stearate (and) PEG-100 stearate[6] | 1 | 1 | 1 | 1 |
| Phenoxyethanol and Methylisothiazolinone[7] | 0.5 | 0.5 | 0.5 | 0.5 |

[1]available from The Dow Chemical Company under tradename UCARE ™ JR-30M
[2]available from Sigma Aldrich under catalog number D4876
[3]available from The Dow Chemical Company under tradename VERSENE ™ 220
[4]available from The Dow Chemical Company under tradename CELLOSIZE ™ PCG-10
[5]available from Croda Inc. under tradename Crodacol CS50
[6]available from Croda Inc. under tradename Arlacel 165
[7]preservative available from The Dow Chemical Company under tradename Neolone ™ PE

Hair Conditioning Performance

Studies to evaluate ease of wet and dry combing of hair treated with a rinse off conditioner formulation of Comparative Examples CF1-CF3 and Example F1 were performed as follows. Slightly bleached caucasian hair from International Hair Importers was used for testing the conditioners. Each tress weighed 2 grams. Each tress was rinsed for 30 seconds under a stream of 40° C. tap water. Using a pipette, 0.4 grams of a solution containing nine percent of sodium lauryl sulfate was applied and lathered through each tress for 30 seconds. The tresses were then rinsed for 1 minute under running water. Excess water was removed from the tresses by passing each tress between the index and middle fingers of the hand. The tresses were then treated with a rinse off conditioner formulation of Comparative Examples CF1-CF3 and Example F1 at 0.4 g formulation/g of hair by massaging the formulation into the wet/damp hair for 1 minute. The tresses were then rinsed for 30 seconds under tap water at 40° C. Excess water was removed by pulling the tresses through the index and middle fingers of the hand. The tresses were placed on a tray covered with paper towels and dried overnight at room temperature.

Coefficient of friction is an industry standard method of measuring reduced frictional properties of treatments on hair and correlates with sensory attributes for smoothness and softness. A Diastron MTT175 tensile tester with 50 g normal force mounted on rubber probe was used for testing in a temperature and humidity controlled room. Two tresses per treatment and five measurements per tress were tested to generate the average friction data reported in Table 2. Coefficient of friction (COF)=F/N, wherein F was the externally applied force and N was the normal force.

TABLE 2

| Rinse off conditioner | COF with direction of scales | COF against direction of scales |
|---|---|---|
| Comparative Example CF1 | 0.70 | 1.38 |
| Comparative Example CF2 | 0.71 | 1.40 |
| Comparative Example CF3 | 0.73 | 1.27 |
| Example F1 | 0.50 | 1.07 |

An INSTRON Model 4464 running BlueHill 2 software was also used for determining conditioning performance by the ease of wet combing and the ease of dry combing. The test employed an INSTRON strain gauge, which was equipped to measure the force required to comb the hair. The conditioning performance was based on the ability of the rinse off conditioner formulation, to reduce the force required to comb the hair with the INSTRON strain gauge. The force was reported as an Average Combing Load (ACL). The lower the number of the ACL value, the better the conditioning effect imparted by the rinse off conditioner formulation tested.

According to the INSTRON wet combing method, hair was first wetted by dipping into distilled water, and then the hair was detangled by combining the tress three times. The tress was then retangled by dipping in distilled water three times. Excess water was removed by passing the tress through the index and middle fingers of the hand twice. The tress was placed on a hanger and INSTRON combed. An average wet combing force from three tresses was measured for each rinse off conditioner formulation. The average wet combing results are provided in Table 3.

According to the INSTRON dry combining method, dry hair was detangled by combining the tress 3 times. Then the hair was retangled by swirling the tress clockwise 3 times and swirling it counterclockwise 3 times. The tress was then placed on a hanger and INSTRON combed. An average dry combining force from three tresses was measured for each rinse off conditioner formulation. The average dry combining results are provided in Table 3.

TABLE 3

| Rinse off Conditioner | ACL (kgf) Dry | ACL (kgf) Wet |
|---|---|---|
| Comparative Example CF1 | 0.045 | 0.87 |
| Comparative Example CF2 | 0.064 | 0.76 |
| Example F1 | 0.028 | 0.19 |

Haft Hydrophobicity

Rinse off hair conditioner prepared according to each of Comparative Example CF2 and Example F1 were tested on two separate 3 g hair samples (Slightly Bleached Caucasian Hair, International Hair Importers, Inc.). The hair samples were first rinsed with water for 30 seconds. Then a 9% w/w aqueous solution of sodium lauryl sulfate was massaged into the hair samples for 60 seconds. Then the hair samples were rinsed with water for 30 seconds. The hair samples were then treated with the rinse off hair conditioner at a dosage of 0.4 g/g or hair and massaged in to the hair for 30 seconds. The hair samples where then rinsed with water for 30 seconds and dried before hydrophobicity testing.

To measure hydrophobicity of the hair, the tresses were combed straight and the tresses were held tightly on both ends with a holder. Ten drops of water were placed at different locations on each tress from the root to the tip. While the water was observed to immediately dissipate into the tress treated with the formulation of Comparative Example CF2, the water continued to bead off of the tress treated with the formulation of Example F1 even after 20 minutes indicating that the rinse off conditioner formulation of Example F1 successfully restored hydrophobicity benefit to the slightly bleached Caucasian hair.

We claim:

1. A hair conditioner formulation, comprising:

a dermatologically acceptable vehicle; and a conditioning polymer, wherein the conditioning polymer is a dextran polymer crosslinked with a dextran crosslinking agent of formula (I)

(I)

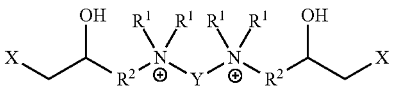

wherein X is a halogen; wherein each $R^1$ is independently selected from a substituted or unsubstituted $C_{1-6}$ alkyl group; wherein each $R^2$ is independently selected from the group consisting of a $C_{1-6}$ alkanediyl group; wherein Y is a divalent bridging group.

2. The hair conditioner formulation of claim 1, wherein the hair conditioner formulation contains less than 0.01 wt %, based on weight of the hair conditioner formulation, of a dermatologically acceptable oil.

3. The hair conditioner formulation of claim 2, wherein the hair conditioner formulation contains less than 0.1 wt %, based on weight of the hair conditioner formulation, of silicon containing molecules.

4. The hair conditioner formulation of claim 3, wherein the hair conditioner formulation is selected from the group consisting of a rinse off conditioner formulation and a leave in conditioner formulation.

5. The hair conditioner formulation of claim 4, wherein the hair conditioner formulation is a rinse off conditioner formulation.

6. The hair conditioner formulation of claim 5, wherein the cationic dextran polymer has a Kjeldahl nitrogen content corrected for ash and volatiles, TKN, of 0.5 to 5.0 wt %.

7. The hair conditioner formulation of claim 6, wherein the dextran crosslinking agent of formula (I) is selected from the group consisting of

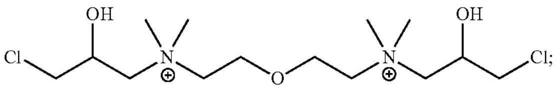

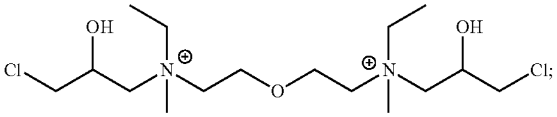

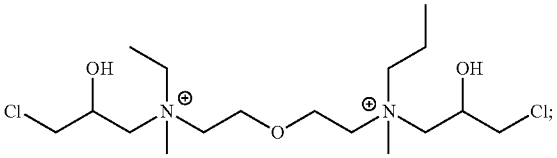

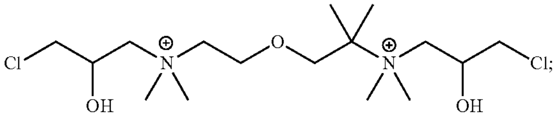

and mixtures thereof.

8. The hair conditioner formulation of claim 7, further comprising a thickener.

9. The hair conditioner formulation of claim 8, further comprising a preservative.

10. A method of conditioning mammalian hair, comprising:

selecting a hair conditioner formulation according to claim 1; and applying the hair conditioner formulation to mammalian hair.

* * * * *